United States Patent [19]

Chou

[11] Patent Number: 5,227,554
[45] Date of Patent: Jul. 13, 1993

[54] ISOMERIZATION PROCESS

[75] Inventor: Tai-Sheng Chou, Pennington, N.J.

[73] Assignee: Mobil Oil Corporation, Fairfax, Va.

[21] Appl. No.: 799,797

[22] Filed: Nov. 29, 1991

[51] Int. Cl.$^5$ .............................................. C07C 5/23
[52] U.S. Cl. ................................... 585/303; 585/301; 585/302; 585/736; 585/738
[58] Field of Search ............... 585/301, 302, 303, 736, 585/738

[56] References Cited

U.S. PATENT DOCUMENTS

| | | | |
|---|---|---|---|
| 2,276,171 | 3/1942 | Ewell | 585/302 |
| 3,020,322 | 2/1962 | Allen | 585/302 |
| 3,224,956 | 12/1965 | Schlinger | 585/302 |
| 4,162,212 | 7/1979 | Miller | 585/302 |
| 4,347,399 | 8/1982 | Rice | 585/738 |
| 4,814,544 | 3/1989 | Olah | 585/747 |
| 4,877,919 | 10/1989 | Schmidt | 585/748 |

OTHER PUBLICATIONS

R. Meyers, Ed. *Handbook of Petroleum Refining Processes*, pp. 5-37 to 5-59 (1986).
N. F. Bland et al., Eds. *Petroleum Processing Handbook*, pp. 3-46 to 3-52 (1967).

*Primary Examiner*—Asok Pal
*Attorney, Agent, or Firm*—Alexander J. McKillop; Malcolm D. Keen; Jessica M. Sinnott

[57] ABSTRACT

A process for the isomerization of $C_4$ and higher molecular weight hydrocarbons, preferably $C_4$ to $C_6$ paraffins with high $C_6$ cyclics content. A $C_5$ to $C_6$ hydrocarbon stream is isomerized in a first isomerization reaction zone and a $C_4$ hydrocarbon stream is isomerized in a second isomerization reaction zone. At least one or both of the effluent streams from the first and second isomerization zones are conveyed to a gas-liquid separator which separates a hydrogen-rich recycle stream. At least a portion of the hydrogen-rich recycle stream is conveyed to the $C_5$ to $C_6$ hydrocarbon feed stream and at least a portion of the hydrogen-rich recycle stream is conveyed to the $C_4$ hydrocarbon feed stream whereby the hydrogen recycle stream is shared during both the $C_4$ isomerization reaction and the $C_5$ to $C_6$ isomerization reaction. The product stream is conveyed to a shared stabilizer which removes the gaseous and volatile components. The product stream can be fractionated to recover the separate $C_4$ to $C_6$ isoparaffins and normal paraffins and naphthenic compounds.

20 Claims, 3 Drawing Sheets

ISOMERIZATION PROCESS

FIELD OF THE INVENTION

The invention is directed to a process for isomerization of $C_4$ and heavier hydrocarbons. More particularly, the invention is directed to isomerizing $C_4$ hydrocarbons separate from the heavier hydrocarbons, i.e $C_5 C_6$, both paraffinic, naphthenic and aromatic, in the presence of an isomerization catalyst and a shared hydrogen recycle stream and product recovery system.

BACKGROUND OF THE INVENTION

Increasing concern about the benzene concentration in gasolines has prompted interest in changing refinery operations by shifting feeds between refinery units to minimize benzene production. By way of example only, the benzene in high benzene content feeds sent to reforming could be separated from the naphthas and routed elsewhere as the benzene passes through the reformer essentially unchanged while the naphthas are converted to higher octane products. It would be more efficient and desirable to remove the benzene from the reformer feed and route it to another process which would convert the benzene to a more agreeable blending component.

The isomerization unit would be suitable because the isomerization unit saturates aromatics to form cycloparaffins which are a preferable gasoline blending component. However, the presence of high levels of $C_6$ hydrocarbons has been found to suppress the isomerization of lower molecular weight hydrocarbons, specifically, the conversion of $C_4$ normal paraffin to isoparaffin. Thus, for purposes of efficiency, processes for the isomerization of $C_5$ and $C_6$ are separated from processes for the isomerization of the $C_4$ hydrocarbons. In isomerization of $C_5$ to $C_6$ hydrocarbons low temperatures (ranging from 110° to 180° C.) favor reaction equilibrium toward higher isoparaffin to total paraffin ratios and avoid cracking. By comparison, in isomerization of butanes, relatively higher temperatures (greater than 150° C.) favor the approach to reaction equilibrium toward higher isobutane to normal butane ratios. Additionally, while the presence of hydrogen is used in isomerization of $C_5$ to $C_6$ hydrocarbons to inhibit side reactions, high concentrations of hydrogen tend to inhibit isomerization of butanes.

In R. A. Meyers, *Handbook of Petroleum Refining Processes*, pp. 5-47 to 5-59 (1986) the UOP Penex process is described as a single-pass isomerization of $C_5$ and $C_6$ hydrocarbons in the presence of hydrogen in a two-stage reactor system using a low temperature noble metal fixed-bed catalyst which works in the presence of a promoter to produce a gasoline blending fraction of about 85 Research Octane Number. A high conversion at a low temperature, i.e. 230° F. to 300° F., is possible. Most of the i-pentane and i-hexanes of isomerization having a high RON are blended into gasoline. A UOP Butamer process is also described in Meyers at pp. 5-39 to 5-46. A fixed-bed vapor phase butane isomerization process is described in which a feedstream rich in $C_4$ hydrocarbons is dried and charged to a one or two isomerization reactor system. The isomerization occurs at a temperature slightly higher than that used in the $C_5$ to $C_6$ isomerization, in the presence of a minor amount of hydrogen. The process converts butanes to isobutanes which are used to make high octane alkylate.

Butane isomerization in the presence of $C_5$ and $C_6$ hydrocarbons in a one or a two-reactor system has been proposed in U.S. Pat. No. 4,877,919 and this process is described as providing the advantages of reduced capital and operating costs associated with separate processing units for butane isomerization and $C_5$ and $C_6$ isomerization while achieving a relatively high across-the-board conversion of the $C_4$ to $C_6$ hydrocarbons. The benefits of using two reactors is described whereby the first reactor operates at higher temperatures to favor butane isomerization and the second reactor operates at a lower temperature to increase the $C_5$ to $C_6$ isoparaffin to total paraffin ratio without reversing isobutane yield. The isomerate product is then transferred to a stabilizer to remove the cracked hydrocarbons containing $C_3$ hydrocarbons and lighter hydrocarbons and excess hydrogen. The patent teaches separating hydrogen from the product stream and recycling it to the $C_4$ to $C_6$ isomerization reaction. U.S. Pat. No. 4,877,919 demonstrates the benefit of isomerization for $C_4$, $C_5$ and $C_6$ normal paraffins. However, there is no discussion of the detrimental effect of $C_6$ cyclics on isobutene yield. $C_6$ cyclics include benzene, cyclohexane, and methyl cyclopentane.

Although it would be advantageous to process $C_4$, $C_5$ and $C_6$ hydrocarbons together through the isomerization reactor, the impact of large amounts (i.e. more than 20%) of $C_6$ hydrocarbons, particularly the $C_6$ cyclics, on the conversion of $C_4$ hydrocarbons detracts from the efficiency of the process. A process for isomerizing $C_4$ and $C_5$ to $C_6$ hydrocarbons separately in two reaction zones without the disadvantages of having entirely separate units would be most practical.

SUMMARY OF THE INVENTION

It is an object of the invention to isomerize $C_4$ hydrocarbons separate from the heavier hydrocarbons without the extra processing equipment required and without the unavoidable reduction in isoparaffin-to-paraffin ratio which occurs when the $C_4$ paraffins are isomerized together with the heavier hydrocarbons with high $C_6$ cyclics.

It is a further object of the invention to isomerize $C_4$ hydrocarbons separate from the $C_5+$ hydrocarbons with a lower overall hydrogen requirement than required for completely separate units.

It is yet another object of the invention to improve upon a method of isomerization of $C_4$ to $C_6$ hydrocarbons.

It is a feature of the invention to isomerize $C_4$ hydrocarbons and $C_5+$ hydrocarbons in parallel reactor systems which permit the sharing of a common hydrogen recycle stream.

It is another feature of the invention to isomerize $C_4$ bons in a reactor system which is separate from a reactor system for isomerization of a higher molecular weight feedstock containing at least 20% $C_6$ hydrocarbons without the disadvantage of suppressing the $C_4$ isomerization and the high cost of operating completely separate isomerization units.

It is an advantage that the isomerization process of the invention has a lower overall hydrogen, process equipment and catalyst requirement.

The invention is directed to a process for isomerizing $C_4$ and heavier hydrocarbons. A first feedstream containing $C_5$ and higher hydrocarbons is isomerized in a first isomerization reaction zone. A second feedstream containing C$_4$ hydrocarbons is isomerized in a second isomerization reaction zone. At least one of the isomerized C$_4$ product stream or the C$_5$+ product stream is conveyed to a high pressure separator which separates a hydrogen-rich recycle stream. At least a portion of the hydrogen-rich recycle stream is recycled to the first feedstream and the second feedstream for use during the isomerization reaction. Thus, the isomerization reactions share a common hydrogen-rich recycle stream. The isomerized product streams are conveyed to a stabilizer section to remove gaseous and low boiling hydrocarbons as by-products of the isomerization reactions. Thereafter, the hydrocarbon product stream is fractionated to recover, at least one C$_4$ hydrocarbon stream and at least one C$_5$+ hydrocarbon stream.

DETAILED DESCRIPTION OF THE INVENTION

The present invention embodies a process for the isomerization of C$_4$ and heavier hydrocarbons (C$_5$+) which comprises the steps of charging a first feedstream containing C$_5$ and higher molecular weight hydrocarbons to a first isomerization reaction zone; charging a second feedstream containing C$_4$ hydrocarbons to a second isomerization reaction zone; contacting the first feedstream admixed with hydrogen in said first isomerization reaction zone with an isomerization catalyst at conditions sufficient to effectuate isomerization to produce a first effluent stream; contacting the second feedstream admixed with hydrogen in said second isomerization reaction zone with an isomerization catalyst at conditions sufficient to effectuate isomerization to produce a second effluent stream; conveying at least one of the effluent streams to a high pressure separator to produce a hydrogen-rich recycle stream; recycling at least a portion of the hydrogen-rich stream for admixture with the first feedstream and the second feedstream whereby a common hydrogen recycle stream is shared during isomerization; conveying the first and second effluent streams to a stabilizer section to remove gaseous and low-boiling components formed during isomerization; and fractionating the product stream to separate the product stream into at least one C$_4$ hydrocarbon stream and at least one C$_5$ and higher molecular weight hydrocarbon stream.

Feedstocks appropriate in the isomerization process include mixtures of butanes, pentanes, hexanes, cyclohexanes, cyclopentanes, and benzenes recovered from hydrocarbon conversion and recovery processes such as crude distillation, fluid catalytic cracking, hydrocracking and coking. The feeds which are usually in the boiling range of C$_4$–200° F. can be used, the butanes being separated from the higher molecular weight hydrocarbons for processing in accordance with the invention. The higher molecular weight feed contains 10 to 70% C$_6$ hydrocarbons preferably 20 to 60% C$_6$ hydrocarbons. The higher molecular weight feed contains C$_6$+ cyclics including benzene, cyclohexane, and methyl-cyclopentane, i.e., containing about 0.5 to 15% C$_6$+ cyclics, preferably ranging from 0.5 to 5% C$_6$+ cyclics, more specifically 0.5 to 3% C$_6$+ cyclics.

Figure 1:
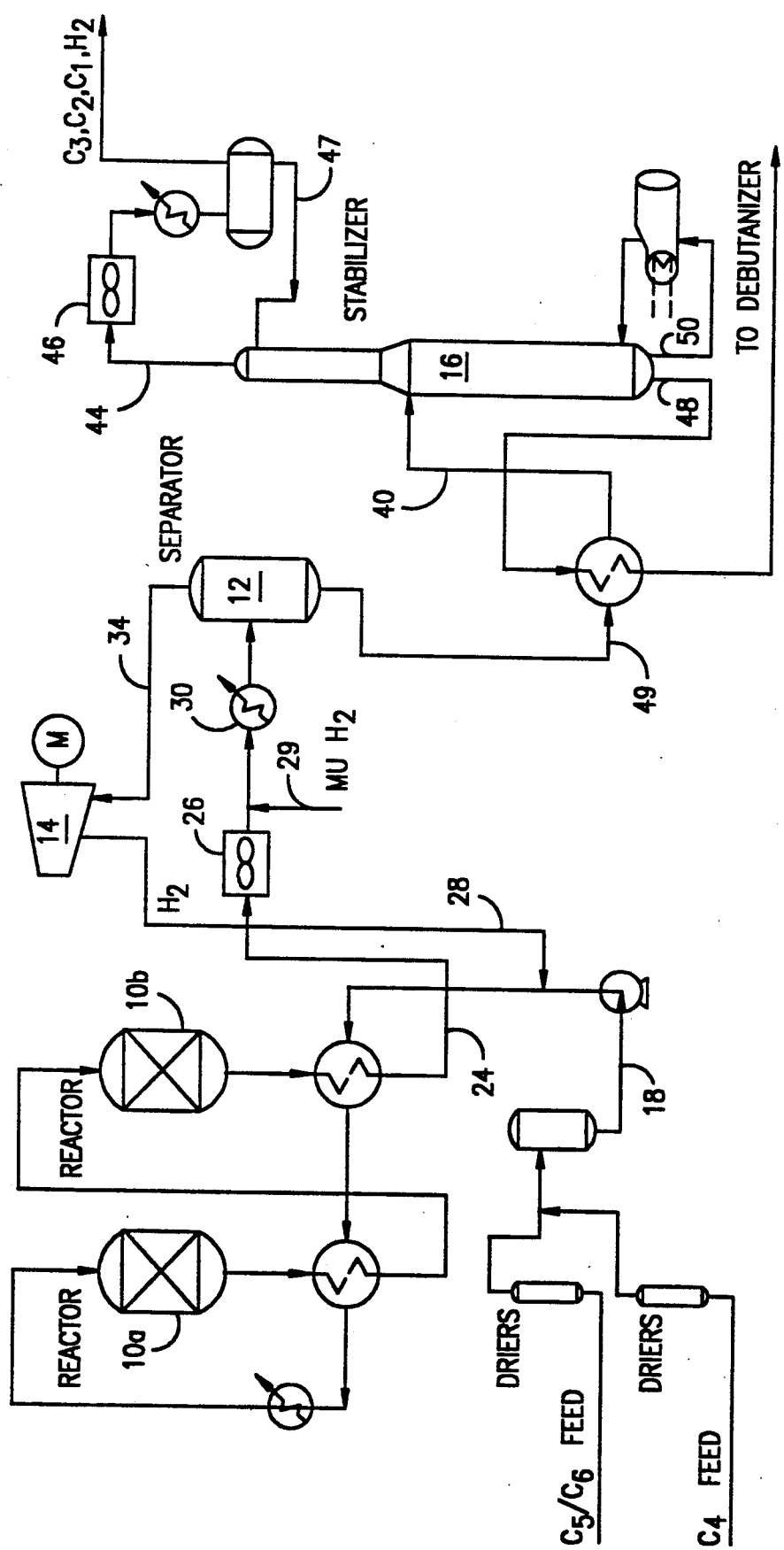
FIG. 1 is a simplified schematic flow diagram of the prior art isomerization process.

In FIG. 1, there is shown the prior art process which includes a high temperature isomerization reactor 10a and a low temperature isomerization reactor 10b, a gas/liquid separator 12, a hydrogen compressor 14 and a stabilizer 16. A dried feedstream containing C$_4$ and higher hydrocarbons is conveyed via line 18 by means of pump 20 to the high temperature isomerization reactor 10a. The high temperature reactor, optimally, has an inlet temperature of about 140° C., ranging from about 130° to about 160° C. and an outlet temperature of at about 170°, ranging from about 160° to about 190° C. The high temperature reactor pressure is maintained at about 380 to 450 psig. The high temperature reactor favors butane isomerization. Thereafter, the feedstream is conveyed to the low temperature isomerization reactor which, optimally, has an inlet temperature of at about 130° C., ranging from about 120° C. to about 145° C. and an outlet temperature of at about 135° C., ranging from about 125° C. to about 150° C. The low temperature reactor favors an increase in the C$_5$ and higher isoparaffin to total paraffin ratio. The low temperature reactor pressure is maintained at about 400 psig, ranging from about 380 psig to 450 psig. Both isomerization reactions are conducted in the presence of hydrogen admixed with the feedstream in a molar ratio of hydrogen to hydrocarbon of about 1.0 to 1.2 ranging from 0.6 to 1.8. The isomerized C$_4$ and higher molecular weight product stream is recovered through line 24 and conveyed to cooler 26 which is preferably an air cooler, and admixed 1 with fresh makeup hydrogen introduced through line 29. The stream is continued through cooler 30, which is preferably a water cooler. The temperature of the stream is thereby reduced to about 38° C. ranging from 35° C. to 45° C. before entering gas-liquid separator 12. In the gas-liquid separator, a hydrogen-rich vapor phase is separated from the liquid phase hydrocarbon stream and recovered through overhead line 34 and is compressed in compressor 14 for recycle through line 28 to the feedstream for use during isomerization.

The C$_4$ and higher molecular weight hydrocarbons in the liquid phase are recovered from the separator 12 and passed to stabilizer 16 via line 40. The stabilizer has a bottom temperature of about 145° C., ranging from 145° C. to about 155° C. and top temperature of about 72° C., ranging from about 72° C. to about 80° C. and is maintained at a pressure of about 312 psig, ranging from 300 psig to 320 psig. An overhead stream is recovered from the stabilizer and passed through air cooler 46 having an outlet temperature of about 31° C., ranging from 28° C. to 38° C. through line 44. The overhead stream contains the gaseous light hydrocarbon by-products of cracking reactions such as C$_3$ and lower molecular weight hydrocarbons and residual hydrogen. A portion of the hydrocarbons are condensed and withdrawn from the top of the stabilizer and recycled back to the stabilizer through line 47. A major portion of the C$_4$ and higher molecular weight hydrocarbons are withdrawn from the bottom of the stabilizer through line 48 passed through heat exchanger 49 and conveyed to a fractionation section.

Figure 2:
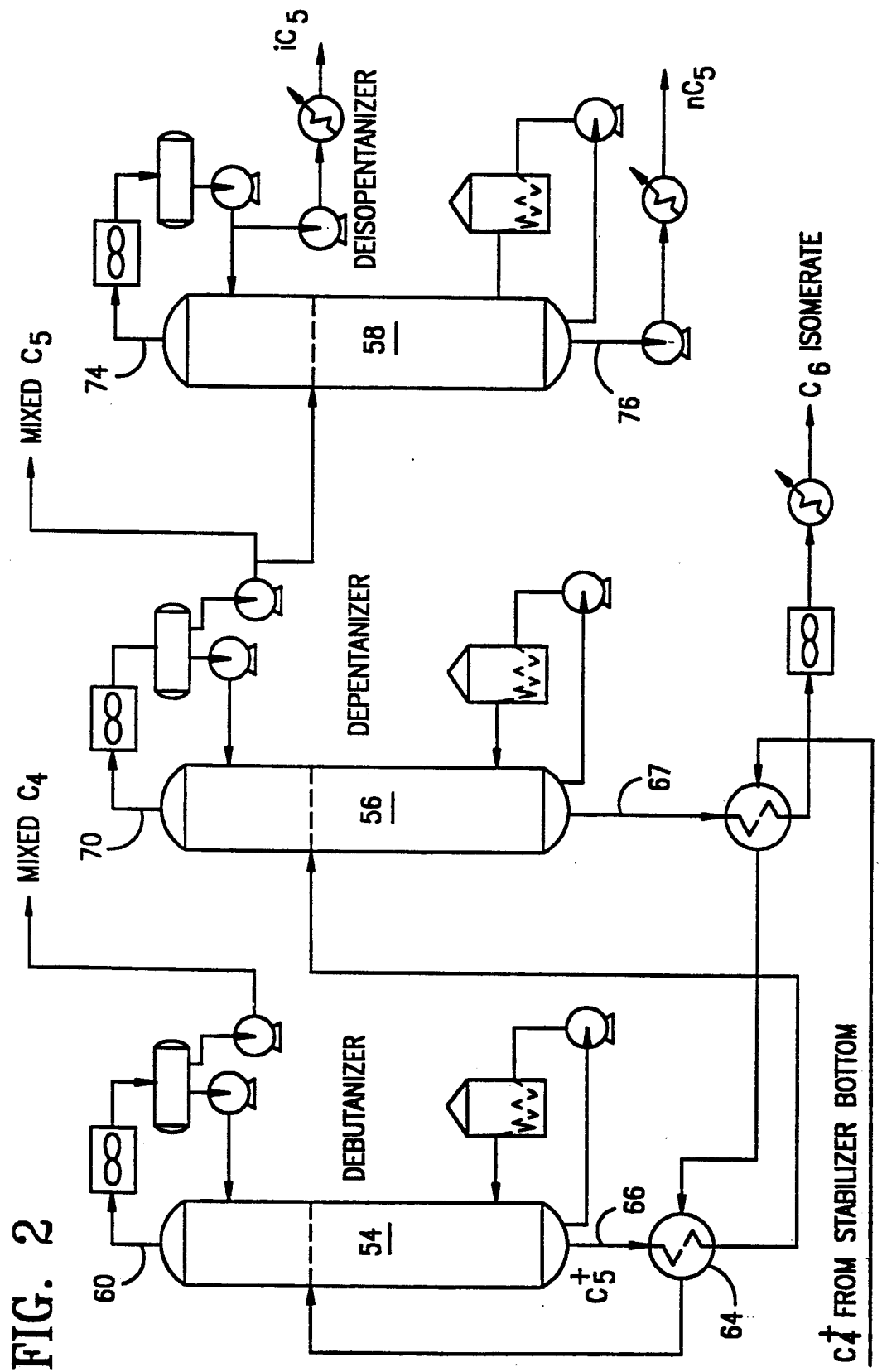
FIG. 2 is a simplified schematic flow diagram of an prior art isomerization fractionation section.

FIG. 2 shows a fractionation section flow diagram which includes a debutanizer 54, depentanizer 56 and deisopentanizer 58. The C$_4$ and higher molecular weight hydrocarbon stream from the stabilizer bottom is charged to the debutanizer 54 which operates at a top temperature of about 84° C., ranging from about 80° C.

to about 90° C., a bottom temperature of about 149° C., ranging from about 145° C. to about 155° C. and pressure of about 160 psig ranging from 150 to 170 psig. A mixed $C_4$ overhead stream is recovered from the top of the debutanizer through overhead line 60. The higher molecular weight hydrocarbons (mixed $C_5$ and higher) are recovered from the bottom of the debutanizer and conveyed through heat exchanger 64 via line 66 to the depentanizer 56. The depentanizer operates at a top temperature of about 97° C., ranging from about 85 C. to 100° C., a bottom temperature of about 133° C., ranging from 120° C. to 135° C. and pressure of about 60 psig to 75 psig. The $C_6$ isomerate is withdrawn from the bottom of the depentanizer through line 67. Mixed $C_5$ hydrocarbons are recovered from the top of the depentanizer and passed through a cooling system via line 70. At least a portion of the mixed $C_5$ hydrocarbons are routed to the deisopentanizer 58 which operates at a top temperature of about 73° C., ranging from 70° C. to 75° C., a bottom temperature of about 95° C., ranging from 92° C. to 98° C. and pressure of about 32 psig to 38 psig. The isopentane is recovered from the top of the deisopentanizer via overhead line 74. The n-pentane is withdrawn from the bottom of the deisopentanizer via line 76.

Figure 3:
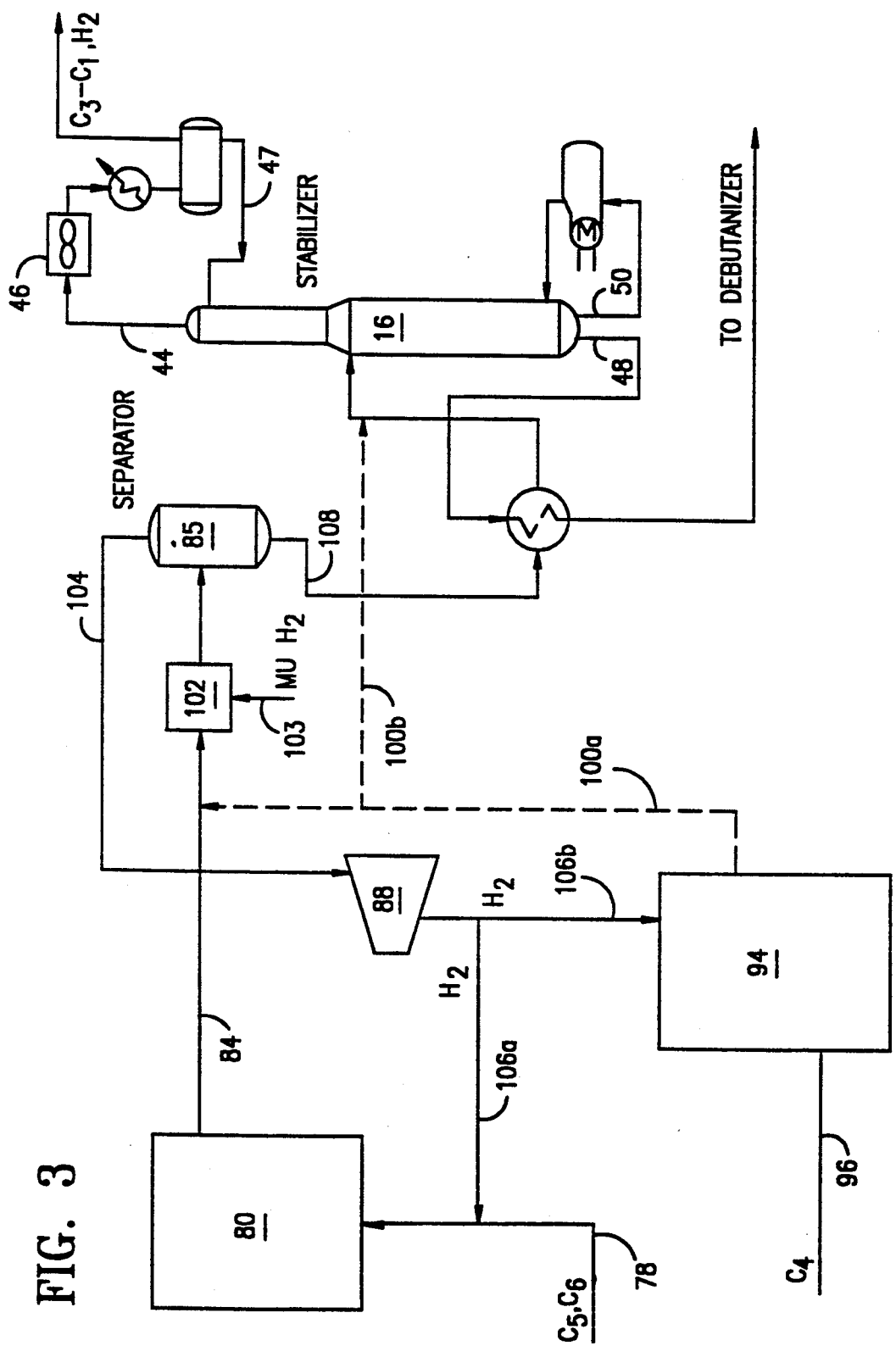
FIG. 3 is a simplified schematic flow diagram of the isomerization process of the invention.

In FIG. 3 the process of the instant invention is shown. There is a first isomerization reaction zone 80, a shared high pressure separator 85, a shared recycle gas compressor 88, a second isomerization reaction zone 94 and a stabilizer 16. In accordance with the invention, a feedstream containing the $C_5$ and higher molecular weight hydrocarbons, preferably $C_5$ and $C_6$ hydrocarbons, is admixed with hydrogen and conveyed through line 78 to the first isomerization zone 80. Because the conversion of $C_5$ and higher molecular weight hydrocarbons will benefit from a relatively high hydrogen concentration, the hydrogen-to-hydrocarbon molar ratio should range from 0.6 to 1.8, preferably 1.0 to 1.2. The isomerization reactor contains a fixed-bed of an isomerization catalyst, preferably a noble metal containing-catalyst. The inlet temperature of the reactor ranges from 130° to 170° C., preferably 130° to 150° C., the outlet temperature ranges from 125° to 150° C., preferably 125° to 140° C. The average temperature ranges from 130° to 170° C., preferably 130° to 145° C. The steam is introduced to the reactor at a liquid hourly space velocity of 0.5 to 2.0, preferably 0.7 to 1.0. A first effluent stream is recovered from the first isomerization zone through line 84.

a feedstream containing $C_4$ hydrocarbons is introduced to the second isomerization reaction zone 94 via line 96. The isomerization reactor contains a fixed-bed of an isomerization catalyst, preferably, a noble metal containing-catalyst which can be the same as the catalyst used in the first isomerization reactor. However, an advantage of the invention is that a different catalyst composition can be used as a catalyst which is more favorable to butane isomerization but less favorable to conversion of $C_5$+ hydrocarbons. The inlet temperature of the reactor ranges from 160° to 190° C., preferably 170° to 185° C., the outlet temperature ranges from 140° C. to 160° C., preferably 145° to 155° C., the average temperature ranges from 150° to 190° C., preferably 150° to 175° C., pressures range from 380 psig to 450 psig, preferably 380 to 420 psig, and LHSV ranges from about 1.5 to 3.5, preferably 2.0 to 3.0. The second effluent is recovered from the second isomerization reaction zone through line 100a. The isomerization is conducted in the presence of hydrogen. Although the $C_4$ conversion favors a relatively lower hydrogen concentration, the hydrogen to hydrocarbon molar ratio in the second reaction zone ranges from 0.01 to 0.8, preferably 0.01 to 0.2.

In one embodiment of the invention, the second effluent, containing $C_4$ hydrocarbons, is combined with the first effluent, containing $C_5$+ hydrocarbons via line 100a. The combined streams are passed through cooling zone 102, which contains at least one cooling unit representative examples of which include a fan cooler and a water cooler, and admixed with make-up hydrogen introduced through line 103. The stream, having a reduced temperature of about 35° C. to 45° C., preferably 36° to 38° C., and pressure of about 380 psig to 450 psig, preferably 400 to 420 psig, is conveyed to the shared gas-liquid separator 85. A hydrogen-rich vapor phase is recovered from the top of the separator via line 104 and introduced to shared recycle gas compressor 88 from which a recycle $H_2$ gas is produced. The recycle $H_2$ gas is recovered from the compressor and is recycled to the first and second isomerization reaction zones via lines 106a and 106b, respectively. From the bottom of shared gas-liquid separator 85 a hydrocarbon product stream is recovered via line 108. The hydrocarbon product stream containing isoparaffins, unreacted normal paraffins, residual hydrogen as well as $C_3$ and lighter hydrocarbons which are by-products of cracking reactions is conveyed to the stabilizer 16 through line 108.

In an alternative embodiment, the second effluent containing $C_4$ hydrocarbons conveyed through line 100a is diverted and routed through line 100b to be combined with the hydrocarbon product stream recovered from the bottom of the high pressure separator 85. The combined stream is transferred to stabilizer 16. This embodiments reduces the demand on the cooling units of cooling zone 102 and shared gas-liquid compressor 88.

Stabilizer 16 stabilizes the isomerate by removing the volatile and gaseous products such as the $C_3$ and lower molecular weight hydrocarbons which are by-products of cracking reactions and residual hydrogen. As described with reference to FIG. 1, the stabilizer has a bottom temperature of about 150° C. and top temperature of about 75° C. and is maintained at a pressure of about 312 psig. An overhead stream is recovered from the stabilizer at the air cooler 46 outlet temperature of about 31° C. through line 44. A portion of the hydrocarbons are removed from the overhead stream and recycled to the stabilizer through line 47. A major portion of the $C_4$ and higher molecular weight hydrocarbons are withdrawn from the bottom of the stabilizer through line 48 passed through a heat exchanger and fractionated into separate product streams. The stabilizer bottoms can be fractionated in any fractionation process known in the art or in a process as described with reference to FIG. 2.

The hydrogen and hydrocarbon feed mixture is contacted in isomerization zones 80 and 94 with an isomerization catalyst. The isomerization catalyst used in the first isomerization zone can be the same or different from the catalyst used in the second isomerization zone. Any catalyst which is known for its ability to isomerize butane and/or higher molecular weight hydrocarbons can be used. Suitable catalyst include Friedel-Crafts type catalyst such as the metallic halide catalyst, i.e, aluminum chloride catalysts. However, active low temperature noble-metal containing hydroisomerization catalysts are preferred. Representative of such catalysts include high chloride catalysts on an alumina support and containing a noble metal. Noble metals can include platinum, palladium, germanium, ruthenium, rhodium, osmium and iridium. Platinum is the most suitable noble metal for the process. The catalyst can contain 0.1 to 0.25 wt. % of the noble metal. The chloride is usually present in an amount ranging from about 2 to about 10 wt.%, preferably about 5%, based upon the weight of the support.

It is desirable to dry the feedstock before contacting it with the catalyst because moisture tends to act as a catalyst poison. Sulfur also acts as a poison, inhibiting noble metal activity. A molecular-sieve feed dryer which can remove the water as well as sulfur is most economically practical. Preferably, the feedstock should contain no more than about 0.5 ppm sulfur. Since water can only be tolerated by the catalyst in a very low concentration the feed should be dried to about 0.1 ppm water or less. Molecular sieve feed-dryers are generally well known in the art and any of a variety of drying processes which can meet the sulfur and water limits can be used. Molecular sieve 13X has been used to absorb sulfur in $C_5+$ hydrocarbons.

Because fluorides are also catalyst poisons and can even poison the molecular sieve feed-dryer, any fluoride present in the paraffins such as paraffins derived from HF alkylation should be treated prior to drying to remove the fluoride.

When utilizing a noble metal-containing high chloride catalyst on an alumina support, the process is most effective if the catalyst operates in the presence of a promoter. Organic chloride promoters are most effective. The promoter maintains a high level of active chloride on the catalyst to replace the chloride which is removed from the catalyst during the isomerization reaction. The amount of promoter in the isomerization recycle gas stream can be maintained at from about 100 to about 500 ppm. Any known organic chloride promoter can be used such as carbon tetrachloride, methylene chloride, 1,1,1-trichloroethane and chloroform can be used.

A multiple-stage reactor is preferred, however, a one-stage reactor can be used. In the multiple stage reactor system there are, preferably, two reactors, a first high temperature reactor and a second low temperature reactor. In the first reaction zone, the high temperature reactor has an inlet temperature ranging from 130° to 160° C., preferably 130° C. The outlet temperature ranges from 125° to 150° C., preferably 135° C.

In the second reaction zone, the high temperature reactor has an inlet temperature ranging from 160° to 190° C., preferably about 180° C. The outlet temperature ranges from 183° to 213° C., preferably 203° C.

In the second reaction zone, the low temperature reactor has an inlet temperature which ranges from about 140° to 155° C., preferably 151° C. and the outlet temperature ranges from 144° to 159° C., preferably 155° C.

The catalyst can be equally distributed between the two reactors of each isomerization zone. The advantage of the multiple-stage reactor system is that it is easier to replace the catalyst without taking the unit off stream. While the catalyst is being replaced in one reactor the entire process stream can flow through one reactor with a minimal impact on the product isoparaffin-to-paraffin ratio. The pressure of each reaction zone is maintained at about 380 psig to 450 psig.

Feed compositions as set forth in the following Table 1 were processed over an isomerization catalyst (UOP I-8). The conversion data, reduced hydrogen and catalyst requirements as set forth in Table 1 obtained from two units operation support the advantages of the invention.

Run 3 of Table 1 represents $C_5/C_6$ isomerization results using the same unit as Run 2. Hydrogen to hydrocarbon molar ratio of 1.76 exceeds that of normal design requirement, due to the reduced hydrocarbon throughput. Normal design requirement for hydrogen recycle system shows about 1.0 hydrogen to hydrocarbon molar ratio. Nevertheless, the reduced catalyst requirement (or higher space velocity) and reduced $H_2$/HC molar ratio for $C_4$ isomerization reaction zone becomes obvious from the tabulated data.

TABLE 1

|  | Run 1 | Run 2 | Run 3 |
|---|---|---|---|
| Feed Components (Vol. %) | | | |
| $C_4$ | 97 | 28.8 | 2.8 |
| $C_5$ | 3 | 38.1 | 51.3 |
| $C_6$ | 0 | 32.5 | 44.0 |
| $C_6$ (cyclics) | 0 | 2.4 | 3.2 |
| $H_2$/hydrocarbon (mole ratio) at reactor inlet | 0.5 | 1.15 | 1.76 |
| LHSV, $hr^{-1}$ | 1.9 | 0.9 | 0.6 |
| First Reactor Temperature (°C.) | | | |
| Inlet | 180 | 155 | 138 |
| Outlet | 203 | 183 | 168 |
| Second Reactor Temperature (°C.) | | | |
| Inlet | 151 | 145 | 118 |
| Outlet | 155 | 150 | 120 |
| Product i $C_4$ yield, % | | | |
| $iC_4/C_4$ | 61 | 37.4 | — |
| Product i $C_5$ yield, % | | | |
| $iC_5/C_5$ | | 77.4 | 78.3 |

What is claimed is:

1. A process for isomerizing $C_4$ and higher molecular weight hydrocarbons, consisting essentially of the steps of:

charging a first feedstream containing $C_5$ and higher molecular weight hydrocarbons and at least 20% $C_6$ hydrocarbons to a first isomerization reaction zone;

charging a second feedstream containing $C_4$ hydrocarbons to a second isomerization reaction zone;

contacting the first feedstream admixed with hydrogen in said first isomerization reaction zone with an isomerization catalyst at conditions sufficient to effectuate isomerization, said conditions including temperatures ranging from about 110° C. to 200° C., pressures ranging from about 380 to 450 psi and a liquid hourly space velocity ranging from about 0.5 to 2.0 to produce a first effluent stream;

contacting the second feedstream admixed with hydrogen in said second isomerization reaction zone with an isomerization catalyst at conditions sufficient to effectuate isomerization, said conditions including temperatures ranging from about 130° C. to 220° C. pressures ranging from 380 to 450 psi and a liquid hourly space velocity ranging from about 0.01 to 0.8 to produce a second effluent stream;

conveying at least one of the effluent streams to a high pressure separator to reduce a hydrogen-rich recycle stream;

recycling at least a portion of the hydrogen-rich stream for admixture with the first feedstream and the second feedstream whereby a common hydrogen recycle stream is shared during isomerization;

conveying the first and the second effluent streams to a stabilizer section to remove gaseous and low-boiling components formed during isomerization; and fractionating the product steam to separate the product stream into at least one $C_4$ hydrocarbon stream and at least one higher molecular weight hydrocarbon stream.

2. The process as described in claim 1 in which the first feedstream contains $C_5$ alkanes, $C_6$ alkanes and $C_5/C_6$ cyclics including aromatic and naphthenic compounds.

3. The process as described in claim 1 in which the liquid hourly space velocity in the second isomerization reaction zone ranges from 2.0 to $3.0^{-1}$.

4. The process as described in claim 1 in which the first and second isomerization reaction zones each include a high temperature reactor and a low temperature reactor.

5. The process as described in claim 4 in which the high temperature reactor of the first isomerization reaction zone has an average temperature of about 140° to about 180° C. and is maintained at pressures ranging from about 380 to about 450 psig.

6. The process as described in claim 4 in which the low temperature reactor of the first isomerization reaction zone has an average temperature of about 125° to about 150° C. and is maintained at pressures ranging from about 380 to about 450 psig.

7. The process as described in claim 4 in which the high temperature reactor of the second isomerization reaction zone has an average temperature of about 170° to about 200° C. and is maintained at pressures ranging from about 380 to about 450 psig.

8. The process as described in claim 4 in which the low temperature reactor of the second isomerization reaction zone has an average temperature of about 145° C. to about 160° C. and is maintained at pressures ranging from about 380 to about 450 psig.

9. The process as described in claim 1 in which the catalyst is a noble metal containing chloride promoted catalyst.

10. In a process of isomerization of $C_4$, $C_5$ and $C_6$ hydrocarbons in which $C_5$ and $C_6$ hydrocarbons are isomerized in the presence of a metallic halide catalyst and hydrogen-to-hydrocarbon molar ratio of about 0.6 to 1.8 and in the absence of $C_4$ hydrocarbons, wherein the improvement, comprising the steps of charging a first feedstream containing $C_5$ and higher molecular weight hydrocarbons and at least 20% $C_6$ hydrocarbons to a first isomerization reaction zone in the presence of hydrogen and with an isomerization catalyst at conditions of temperature and pressure sufficient to effectuate isomerization whereby a first effluent stream is produced;

charging a second feedstream containing $C_4$ hydrocarbons to a second isomerization reaction zone in the presence of hydrogen and an isomerization catalyst at conditions of temperature and pressure sufficient to effectuate isomerization whereby a second effluent stream is produced;

conveying the first and second effluent streams to a high pressure separator to produce a hydrogen-rich recycle stream and a product stream containing $C_4$, $C_5$ and higher molecular weight hydrocarbons;

recycling at least a part of the hydrogen-rich recycle stream for admixture with the first feedstream and the second feedstream whereby a common hydrogen-rich recycle stream is shared during isomerization;

conveying the product stream to a stabilizer section to remove gaseous and low-boiling components formed during isomerization; and fractionating the product stream to separate the product stream into at least one $C_4$ hydrocarbon stream and at least one higher molecular weight hydrocarbon stream.

11. The process as described in claim 10 in which the first feedstream contains $C_5$ alkanes, $C_6$ alkanes and $C_5/C_6$ cyclics including aromatic and naphthenic compounds.

12. The process as described in claim 10 in which the liquid hourly space velocity in the second isomerization reaction zone ranges from 1.5 to $3.5^{-1}$.

13. The process as described in claim 10 in which the first and second isomerization reaction zones each include a high temperature reactor and a low temperature reactor.

14. The process as described in claim 13 in which the high temperature reactor of the first isomerization reaction zone has an average temperature of about 140° to about 180° C. and is maintained at pressures ranging from about 380 to about 450 psig.

15. The process as described in claim 13 in which the low temperature reactor of the first isomerization reaction zone has an average temperature of about 125° to about 150° C. and is maintained at pressures ranging from about 380 to about 450 psig.

16. The process as described in claim 13 in which the high temperature reactor of the second isomerization reaction zone has an average temperature of about 170° to about 200° C. and is maintained at pressures ranging from about 380 to about 450 psig.

17. The process as described in claim 13 in which the low temperature reactor of the first isomerization reaction zone has an average temperature of about 145° to about 160° C. and is maintained at pressures ranging from about 380 to about 450 psig.

18. An integrated process of isomerization of $C_4$, $C_5$ and $C_6$ hydrocarbons in which the $C_4$ hydrocarbons are isomerized in the absence of the $C_5$ and $C_6$ and higher molecular weight hydrocarbons, comprising the steps of:

charging a first feedstream containing $C_5$ hydrocarbons and at least 20% $C_6$ hydrocarbons to a first isomerization reaction zone in the absence of $C_4$ hydrocarbons and in the presence of hydrogen and an isomerization catalyst at conditions of temperature and pressure sufficient to effectuate isomerization whereby a first effluent stream is produced;

charging a second feedstream containing $C_4$ hydrocarbons to a second isomerization reaction zone in the absence of $C_5$ and $C_6$ and higher molecular weight hydrocarbons and in the presence of hydrogen and an isomerization catalyst at conditions of temperature and pressure sufficient to effectuate isomerization whereby a second effluent stream is produced;

separating a hydrogen-rich recycle stream from the first effluent stream;

recycling at least a part of the hydrogen-rich recycle stream for admixture with the first feedstream and the second feedstream whereby a common hydrogen-rich recycle stream is shared during isomerization providing an integration of the C$_4$ isomerization and the C$_5$ and C$_6$ isomerization steps which reduces overall hydrogen requirements;

conveying the first and second effluent streams to a stabilizer section to remove gaseous and low-boiling components formed during isomerization and produce a product stream containing C$_4$, C$_5$ and C$_6$ hydrocarbons; and fractionating the product stream to separate the hydrocarbons into at least one C$_4$ hydrocarbon stream and at least one stream containing higher molecular weight hydrocarbons.

19. The process as described in claim 18 in which the liquid hourly space velocity in the second isomerization reaction zone ranges from 1.5 to 3.5$^{-1}$.

20. The process as described in claim 18 in which the first and second isomerization zones each include a high temperature reactor and a low temperature reactor, the high temperature reactor of the first isomerization reaction zone having an average temperature of about 140° C. to about 180° C. and maintained at pressures ranging from about 380 to about 450 psig, the lower temperature reactor of the first isomerization reaction zone having an average temperature of about 125° to about 150° C. and is maintained at pressures ranging from about 380 to about 450 psig, the high temperature reactor of the second isomerization reaction zone having an average temperature of about 170° to about 200° C. and is maintained at pressures ranging from about 380 to about 450 psig, and the low temperature reactor of the second isomerization reaction zone having an average temperature of about 145° C. to about 160° C. and is maintained at pressures ranging from about 380 to about 450 psig.

* * * * *